(12) United States Patent
Waelti et al.

(10) Patent No.: US 8,049,899 B2
(45) Date of Patent: Nov. 1, 2011

(54) METHOD AND APPARATUS FOR DETERMINATION OF GEOMETRIC VALUES ON A TRANSPARENT OR DIFFUSIVE OBJECT

(75) Inventors: Rudolf Waelti, Schwarzenburg (CH); Urs Buri, Maus (CH); Jörg Breitenstein, Bern (CH)

(73) Assignee: Haag-Streit AG, Koniz (CH)

( * ) Notice: Subject to any disclaimer, the term of this patent is extended or adjusted under 35 U.S.C. 154(b) by 740 days.

(21) Appl. No.: 12/083,004

(22) PCT Filed: Nov. 8, 2006

(86) PCT No.: PCT/CH2006/000625
§ 371 (c)(1),
(2), (4) Date: Apr. 2, 2008

(87) PCT Pub. No.: WO2007/053971
PCT Pub. Date: May 18, 2007

(65) Prior Publication Data
US 2009/0268209 A1    Oct. 29, 2009

(30) Foreign Application Priority Data
Nov. 10, 2005  (EP) .................................. 05405625

(51) Int. Cl.
*G01B 9/02* (2006.01)
(52) U.S. Cl. ..................................... 356/497
(58) Field of Classification Search .............. 356/479, 356/497
See application file for complete search history.

(56) References Cited

U.S. PATENT DOCUMENTS

| | | | |
|---|---|---|---|
| 5,301,010 A | 4/1994 | Jones et al. | |
| 5,325,134 A | 6/1994 | Kohayakawa | |
| 5,684,562 A | 11/1997 | Fujieda | |
| 6,198,540 B1 | 3/2001 | Ueda et al. | |
| 6,755,819 B1 * | 6/2004 | Waelti | 606/5 |
| 6,806,963 B1 * | 10/2004 | Walti et al. | 356/497 |
| 2005/0140981 A1 * | 6/2005 | Waelti | 356/479 |

FOREIGN PATENT DOCUMENTS

| | | |
|---|---|---|
| DE | 3446014 A1 | 6/1986 |
| DE | 251 497 A1 | 11/1987 |
| DE | 43 25 494 A1 | 7/1994 |
| WO | WO-96/35100 A1 | 11/1996 |

(Continued)

*Primary Examiner* — Hwa Lee
(74) *Attorney, Agent, or Firm* — Birch, Stewart, Kolasch & Birch, LLP

(57) ABSTRACT

A Michelson-interferometer which has two reference arms and a short coherence length is used for the method and apparatus for measurement of geometric values on transparent or diffuse objects (19). The basic optical delay times of the reference arms (11, 12) are chosen in such a manner that they result in an optical delay time difference corresponding to a layer thickness, as a geometric value. The at least two reference arm beams (33a, 35a) are passed to a single rotating path-length variation element (23), with a mutual spatial offset angle (dw). A delay-time change, which is dependent on the rotation angle, of the reference arm beams is produced as a function of a rotation angle caused by rotation, in order to allow a delay-time change caused by the path-length variation element (23) to be applied successively to the basic optical delay times in the reference arms (11, 12). A topography as a further geometric value is obtained by projection of a light-intensity structure onto a surface to be measured, and by measurement of its image.

15 Claims, 6 Drawing Sheets

FOREIGN PATENT DOCUMENTS

| WO | WO-01/38820 A1 | 5/2001 |
| WO | WO-03/062802 A2 | 7/2003 |
| WO | WO-03/086180 A3 | 10/2003 |
| WO | WO-2004/043245 A1 | 5/2004 |

* cited by examiner

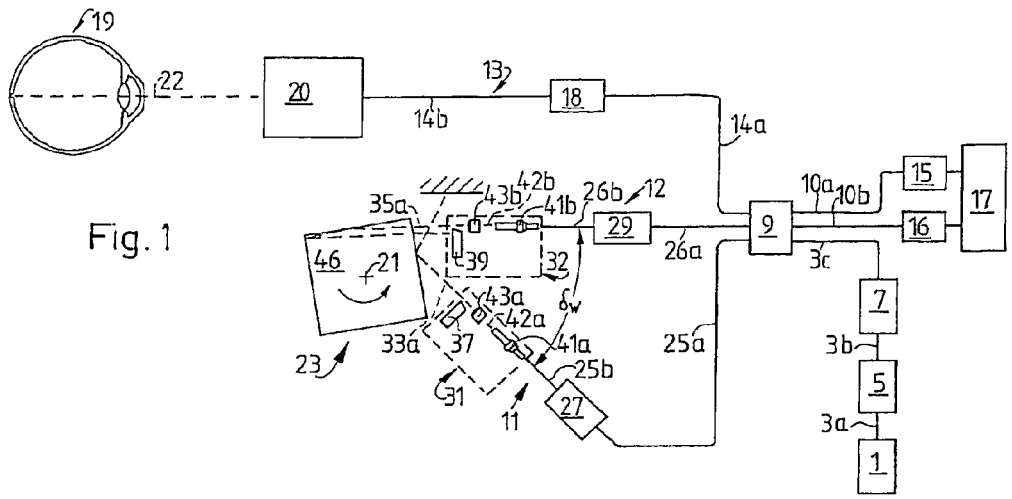
Fig. 1
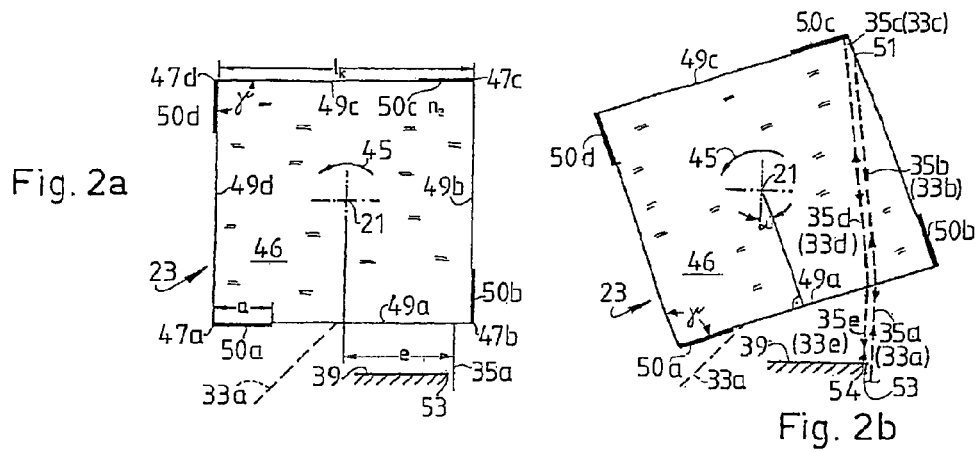
Fig. 2a
Fig. 2b
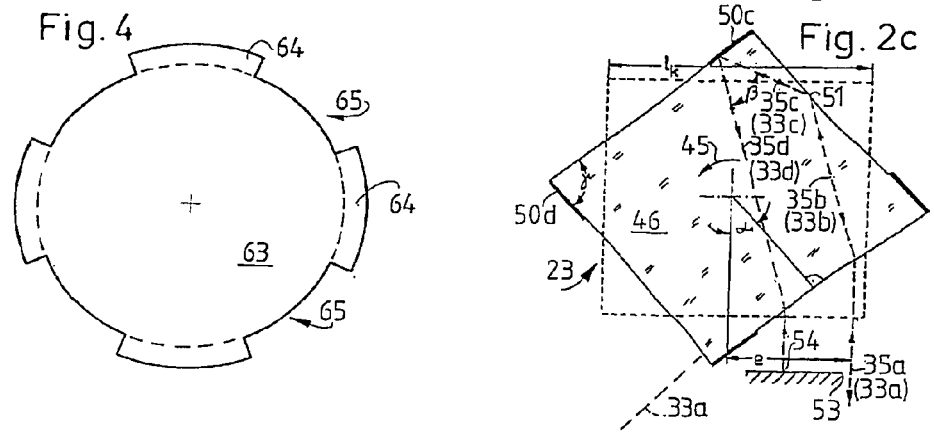
Fig. 4
Fig. 2c

METHOD AND APPARATUS FOR DETERMINATION OF GEOMETRIC VALUES ON A TRANSPARENT OR DIFFUSIVE OBJECT

TECHNICAL FIELD

The invention relates to a method and an apparatus for determination of geometric values of at least two regions, spaced apart from one another, in the case of a transparent or diffusive object, in particular for determination of layer thicknesses and lengths and/or surface curvatures (topography) as geometric values. Geometric values are understood, for example, as layer thicknesses, distances, lengths and topographies.

PRIOR ART

Time Domain Optical Coherence Tomography ("TDOCT") systems generally operate by shifting a time window. In the case of such a conventional system, the length of a reference arm of a Michelson interferometer is moved in accordance with a length to be measured on a measurement object. An interference phenomenon occurs in the detector arm of the Michelson interferometer whenever the delay time of a radiation in the measurement arm is equal to a radiation delay time in the reference arm. A single detector is required in order to detect this interference phenomenon in the case of the known apparatuses.

An alternative to the TDOCT reference arm of variable length is to measure a spectral density in a Michelson interferometer by using a spectrometer, in which case the term Spectral Domain Optical Coherence Tomography ("SDOCT") is used. There is no need in this case to undertake to vary the length of the reference arm. Use is made merely of a unit that causes a phase shift. The radiation split by the spectrometer in the spectral region is then guided to a row of detectors, and the electrical signals thus obtained are evaluated by Fourier transformation.

Optical thicknesses could be determined quickly and accurately with Michelson interferometers by using TDOCT. Known Michelson interferometers had a measurement arm and a reference arm. The optical arm length of the reference arm could be varied in accordance with the measurement lengths in the measurement arm, for example by displacing a retroreflector. Known Michelson interferometers furthermore had a radiation source whose radiation was split into the measurement arm and into the reference arm. The object (measurement object) for which geometric values such as, for example, a layer thickness, a length or a topography were to be determined was arranged in the measurement arm. The beams reflected by the object and by a mirror in the reference arm were superposed. Interference between the reflected beams by the front side and by the rear side of the layer occurred whenever the optical delay times of the radiations were equally long in the measurement arm and in the reference arm. Use was preferably made of a radiation source of short coherence length. The displacement path of the mirror or some other defined optical delay time variation in the reference arm then specified the respective layer thickness through taking account of the refractive index of the layer.

When the aim was to determine exact layer thicknesses from approximately known layer thicknesses as in the case of the human eye, for example, the reference arm was split into two partial reference arms in order to reduce the measurement time and to rule out incorrect measurements by non-defined reflection points. A first optical reference arm length then defined an optical delay time up to the layer surface, and a second optical reference arm length defined the optical delay time up to the "standardized" layer underside. It was thus only the deviations from the "standard" that were determined. These two partial reference arms were shown, for example, by FIG. 12 in U.S. Pat. No. 5,301,010. However, it was also possible to use a single reference arm that had two mirrors offset in the beam direction and designed as a stepped mirror; such an arrangement was shown by U.S. Pat. No. 5,301,010, for example in FIG. 9.

However, it was also possible to undertake a partial beam deflection in the measuring beam with the same result, as described in WO 01/38820. In WO 01/38830, a direct first measuring beam was focused onto the rear side of the layer, for example. A second measuring beam, partially masked out of the first measuring beam, was deflected via a detour and focused in the detour in such a way that its focal point came to lie approximately on the front side of the layer. The detour length then corresponded to the standard layer thickness to be expected. Only a single reference arm with a path variation element was then present.

A coherence tomograph having a number of reference arms is known from U.S. Pat. No. 6,198,540 (Kowa). A beam splitter produces for the reference arms a number of different optical paths in which the path length can be varied with the aid of suitable means. One of the embodiments exhibits a packet of disks that are arranged in parallel next to one another and have a respectively spirally running, reflecting lateral surface and a diameter differing from disk to disk. Rotating the disk packet varies the path length continuously during a rotation. The reference beams directed parallel to one another onto the different spiral disks permit the implementation of fundamental delay times that are simultaneously different, the fundamental delay times being continuously varied by the rotating spiral disks during a revolution.

WO 03/086180 (Haag-Streit) discloses, as part of the opthalmological examination and/or treatment station, a measuring arrangement that has a Michelson interferometer with a short coherence radiation source. An optically transparent and/or diffusive, reflecting object can be brought into the measurement arm, and a rotating cube can be brought into the reference arm (5) as a path length variation unit for changing delay time. Furthermore, at least two reflectors causing a delay time difference are present. The measuring arrangement serves the purpose of measuring optical properties of at least two spaced apart regions in the case of the transparent and/or diffusive object with a measurement time in the sub-second range.

The arrangements described above for determining layer thickness are complicated optical arrangements.

SUMMARY OF THE INVENTION

Object of the Invention

It is an object of the invention to present a method and an apparatus in the case of which geometric values on transparent and/or diffusive objects can be determined in a compact, relatively simple arrangement with little outlay on adjustment.

Achievement of the Object

The object is achieved by the features of claim 1 and of claim 6. A Michelson interferometer known per se is used as a time domain optical coherence tomograph with at least two reference arms of different optical length for the purpose of determining layer thicknesses, a difference in the optical path length in the at least two reference arms corresponding to a "standard" layer thickness at or in a transparent or diffusive object. A standard layer thickness is understood as a layer thickness whose general layer thickness is certainly known, but what is an issue is deviations from this generally known layer thickness that are to be determined. The radiation emanating from the radiation source of the Michelson interferometer has a short coherence length by comparison with the layer thicknesses to be measured.

In the case of the human eye, for example, generally known layer thicknesses are the thickness of the cornea, the depth of the anterior chamber, the lens thickness and the vitreous body depth, or combinations thereof; of course, it is also possible to determine lengths, such as the eye length. In addition to layer thicknesses in organic objects, it is also possible to determine layer thicknesses of inorganic material such as, for example, film thicknesses, coating thicknesses, etc. The Michelson interferometer, known per se, now has a rotating path variation element as described, for example, in EP 0 877 913 and DE 34 46 014.

By contrast with the known Michelson interferometers having at least two reference arms, this one rotating path length variation element is now active part in the at least two reference arms, the path length changes produced by the path length variation element preferably running over regions of equal length. The beams of the two reference arms are now not guided in parallel, but at an offset angle (that is to say obliquely) from one another onto this one path length variation element in such a way that the path length variation acts initially in one reference arm and then in the other reference arm. Owing to this sequential action, the interferences corresponding to the front side and the rear side of the layer (or to the start of a separation and the end of a separation) can be satisfactorily separated from one another, since they always occur in a fashion following one another in time. The alignment of the at least two reference arms and of the rotating path length variation element can now further be undertaken in such a way that there is produced for the purpose of separating the two signals from the at least two reference arms an interruption in which no reflection of radiation occurs in the reference arms over a prescribed time period.

The rotation axis of the path variation element is preferably arranged parallel to the plane lateral surfaces, the or each reference beam striking the relevant lateral surface in a fashion perpendicular to the rotation axis (that is to say in a geometric plane perpendicular to the rotation axis). There is no need for each reference beam to be guided in such a way; oblique impingement angles (that is to say ones differing from 90°) are also possible, which would render the path length variation length variable. However, determining the path length variations to be achieved and their change in path length running as linearly as possible over the rotational angle can be designed and calculated most simply given an arrangement perpendicular to the axis.

The radiations in the measurement and in the reference arms are always guided as far as possible in radiation conductors. It is necessary to couple out of and into radiation conductors only upstream and downstream of the path variation element and of the measurement object and other optical components. The use of radiation conductors as far as possible on the entire path in the measurement arm and the paths in the reference arms permits a robust and interference-free design of the apparatus. Consequently, a beam is spoken of in the description below whenever what is involved is radiation that is not guided in a radiation conductor and is thus in free space and exhibits just a beam configuration; radiation is spoken of in the radiation conductors.

In order to obtain distinct interference signals even given only weakly reflecting top sides and undersides of the layers in the measurement arm, the measurement radiation in the measurement arm is focused onto the top side or underside of the layer. The measurement method is very sensitive; the aim is to reflect at least $10^{-4}$% of the radiation intensity respectively falling onto the top side or underside of the layer. However, this focusing must be performed synchronously or periodically with the rotation of the path length variation element. That is to say, whenever, for example, one reference arm measures the top side of the layer together with the path length variation element, there is also a need to focus the measuring beam onto the top side of the layer, and when the other reference arm then subsequently measures the underside of the layer the measuring beam must be focused onto the underside of the layer.

It may be remarked to this end that the path variation element described in detail in EP 0 877 913 has a square cross section and, for example, is operated at a rotation frequency of 2.5 Hz, in which case, as described below, a switchover frequency of 20 Hz results for the focal points in the case of just two reference arms.

Instead of a square cross section in which the reference radiation runs, it is also possible, of course, to use other regular polygons as cross section. In addition to regular polygons as cross section, it is also possible, analogously as in DE 34 46 014, to use star-shaped cross sections with external silvering.

Although the cross section is generally designed as a regular polygon, this need not be so. It is also possible to use irregular polygons. In this case, however, a variation path superposed on the fundamental path of the reference arm is of different length through a specific polygonal surface, depending on the radiation entrance, something which is not necessarily a hindrance, since the respective variation path length is stored in a fashion combined with the respective rotational angle. An irregular star of DE 34 46 014 can also be used by analogy.

A displacement of the focal point can now be performed by an appropriate displacement of a focusing lens. Displacing a lens now has the disadvantage that the lens must be displaced precisely on the beam axis, as otherwise a lateral displacement (tilting) arises between the measurement points on the top side and underside of the layer; "oblique" layer thicknesses would be measured.

It is now proposed here not to displace the focusing lens, but to introduce into the nonparallel beam path upstream or downstream of a corresponding focusing lens a transparent material of prescribable thickness and with the prescribed refractive index. If the material has been introduced in the beam path, a displaced focal point results by comparison with material removed from the beam path. It would now be possible to push through the beam path at an appropriate speed a transparent "comb" with plane parallel comb teeth, in which case the comb teeth would then define a focal point position, and the interspaces would define another displaced focal point position. If three and more different focal points are required, the comb teeth could be designed in a stepped fashion, also with different thicknesses and plane parallel front and rear sides in each case.

However, the use of a linear displacement has the disadvantage that after having passed through once the comb must be moved in the opposite direction with an appropriate acceleration at the reversal point, and this would occasion different widths and spacings of the teeth. For this reason, it will be advantageous to use a rotating disk with a rectangular tooth system for a rapid displacement of focal point, the tooth regions being selected to be transparent with an appropriate refractive index and with appropriate thickness.

The determination of thickness outlined above can be carried out as described. However, the layers to be measured are frequently not plane. A typical example of this is the cornea of the human eye. In addition to the eye length, the thickness of the cornea or of the crystalline lens, it is now particularly important to determine the surface curvature of the latter at the same time for providing eye treatment.

In order to be able, in addition to the simple linear measurements outlined above (for example thickness measurement), also further to determine the topography as a further geometric value at the same time, an optical structure produced by different luminances is used upstream of the object to be measured, in this case the eye. The radiation of this structure is reflected by the eye surface and imaged and the image is evaluated. Since the generally flat structure arranged upstream of the object is known, it is possible to infer the curvature from the image.

The determination of layer thicknesses and lengths, as well as the determination of the topography, is performed optically. It is now to be ensured that there is no mutual interference between the radiations used for the optical methods. It will now be possible in the case of the two methods of determination to modulate different modulation frequencies onto the radiations, or to operate with different polarization. However, it is preferred to operate with different radiation wavelengths. In order to be able to superpose beams of different wavelengths, use is made of a wavelength-selective mirror that deflects one radiation by reflecting it, and transmits the other radiation without loss, as far as possible. It is preferred to deflect the measuring beam of the Michelson interferometer by reflecting it, and to allow transmission of the radiation for the purpose of determining the topography. It would, of course, also be possible to proceed inversely.

The optical structure to be arranged upstream of the surface to be measured can be a Placido disk, which has long been known. However, it is preferred to use radiation sources arranged in a prescribed structure. The way in which it is possible to infer the surface curvature from the spatial structure of the light sources is described, for example, in DE 43 23 494, U.S. Pat. No. 5,325,134, DE 251 497, U.S. Pat. No. 5,684,562, in the publication by M. R. Morelande et al., "Automatic Estimation of the Corneal Limbus in Videokeratooscopy", IEEE 2002, pages 1617-1625 and Trans. on Biomedical Eng., vol. 49, no. 12, Dec.

It is preferred to use LEDs as radiation sources. A diffusing screen can be placed upstream of the LEDs in the beam path in order to be able to determine a centroid of the radiation (light) spot effectively during evaluation. In addition, LEDs of different wavelengths can be used in order, for example, in the case of severely deformed corneas in the case of whose measurement a number of LED images could overlap, to obtain a unique assignments of the LEDs to their images. The use of a diffusing screen has the further advantage that it is possible to use LEDs of a larger radiance (luminance) than without diffusing screen.

Instead of operating the Michelson interferometer as a time domain optical coherence tomograph (TDOCT), it can also be operated in a converted fashion as a spectral domain optical coherence tomograph (SDOCT). An SDOCT is a very quick measuring instrument, and it is therefore suitable, in particular, for processing many measurement points that occur, for example, during the determination of a topography or a three-dimensional tomography. Thus, as set forth below, instead of using a number of LED radiation sources as outlined above, it is also possible to determine a topography with the aid of SDOCT.

Further variations of the design of the invention and their advantages emerge from the following text.

BRIEF DESCRIPTION OF THE DRAWINGS

Examples of the inventive apparatus and of the inventive method are explained in more detail below with the aid of drawings, in which:

FIG. 1 shows a schematic of an inventive apparatus for determining thicknesses and/or path lengths in optically transparent and/or diffusive materials, FIGS. 2a-c show a path length variation element, rotatable about a rotation axis, of the apparatus illustrated in FIG. 1, FIG. 4 shows a focal point displacement unit as a rotating disk for adjusting the focal point of a measuring beam of the apparatus illustrated in FIG. 1, FIGS. 5a-d show a design variant of the focal point displacement unit illustrated in FIG. 4, which is assembled from two rotating disks, in which case

WAYS OF IMPLEMENTING THE INVENTION

Figure 3:
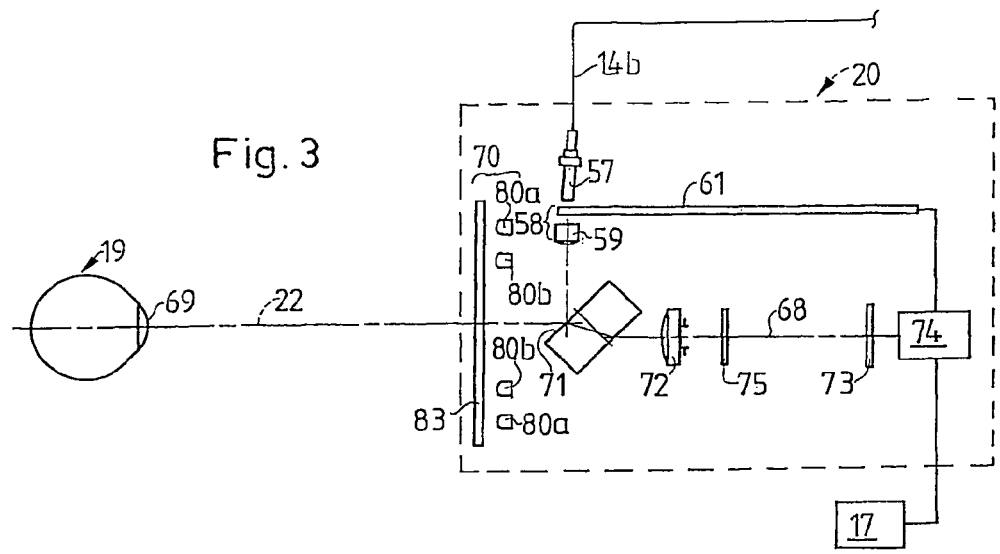
FIG. 3 shows a sketch of a measuring head of the apparatus illustrated in FIG. 1.

An exemplary embodiment of the inventive apparatus with an optical arrangement of the type of the "Michelson interferometer" is illustrated in FIG. 1. In the optical arrangement of the type of the "Michelson interferometer", the apparatus has a radiation source 1 whose radiation has a short coherence length. The coherence length is substantially shorter than the thicknesses and path lengths to be measured and lies in the range of 2 µm to 100 µm. It is normal to work in a range of 10 µm to 20 µm. The shorter the coherence length, the more accurately it is possible to measure. A radiation source 1 with an output radiation as broadband as possible will therefore be selected. A super luminescent diode (SLD), a light emitting diode (LED), a white light source or a light source with amplified spontaneous emission (ASE), for example the radiation of a diode-pumped solid) can be used as radiation source 1. This radiation is coupled into a monomode fiber 3a.

The monomode fiber 3a is guided to a radiation attenuator 5. The radiation attenuator 5 can be, for example, a loss splice between two monomode fibers (not illustrated). The radiation attenuator 5 can undertake to attenuate the radiation retroreflected by the reference arms and the measurement arm, which are described below, in the direction of the radiation source 1. By way of example, in the case of an SLD, an ASE or a diode-pumped solid radiation retroreflected into the radiation source 1 could have a negative influence on the emission behavior. The radiation attenuator 5 thus serves to minimize this negative influence. The now possibly attenuated radiation of the radiation source 1 is guided from the radiation attenuator 5 into a monomode fiber 3b leading to a polarization controller 7. The polarization state of the radiation that traverses the controller is set with the aid of the polarization controller 7. The radiation attenuator 5 and the polarization controller 7 are optional, and are not mandatory for the inventive apparatus.

The radiation of the radiation source 1 is, furthermore, guided by means of a monomode fiber 3c on to a 3×3 monomode fiber coupler 9. The monomode fiber coupler 9 is used to split the radiation of the radiation source 1 into two reference arms 11 and 12 and into a measurement arm 13. The two remaining outputs of the 3×3 monomode fiber coupler 9 are respectively connected to a detector 15 or 16 by means of a respective radiation conductor 10a and 10b that, for its part, is connected to detection electronics 17. The detector 15 detects interference between the radiation reflected by the measurement object 19 and reflected radiation in the reference arm 12. The detector 16 measures interference between the radiation reflected by the measurement object 19 and reflected radiation in the reference arm 11.

The measurement arm 13 has a monomode fiber 14a of which one end is connected to the monomode fiber coupler 9. The other end of the monomode fiber 14a is connected to a polarization controller 18 from which a further monomode fiber 14b is guided to a measuring head 20 that is described in more detail below. The radiation then proceeds from the measuring head 20 as a free space beam 22 to the measurement object 19 (here an eye).

The reference arms 11 and 12 have a different fundamental optical path length in accordance with a layer thickness or length to be measured in or on the measurement object 19. One and the same path length variation element 23 which can rotate about an element axis 21, acts in both reference arms 11 and 12.

The reference arms 11 and 12 are connected with the 3×3 monomode fiber coupler 9 by a respective monomode fiber 25a or 26a. The end of the monomode fiber 25a or 26a respectively averted from the monomode fiber coupler 9 is connected to a polarization controller 27 or 29. One monomode fiber 25b or 26b each is guided from the respective polarization controller 27 or 29 to an optical unit 31 or 32 that respectively converts the radiation guided inter alia in the monomode fiber 25b or 26b into a free space beam 33a or 35a. The two free space beams 33a and 35a are guided onto the path length variation element 23 at a mutual offset angle $\delta_w$ (thus not in parallel), and are guided by the path length variation element 23, if, as described below, the latter has a specific rotary position, onto in each case one mirror 37 or 39 in the optical unit 31 or 32 and reflected back again by the latter into the monomode fiber 25b or 26b via the path length variation element 23. Up to an angular tolerance, the offset angle $\delta_w$ is half as large as a corner angle γ of the path length variation element 23. The selected angular tolerance influences the available path length variation length. The larger the angular tolerance selected, the smaller becomes the path length variation length. Since a square cross section of the path length variation element 23 has been selected in the example chosen here, the offset angle $\delta_w$ is 45°. The path length variation element 23 selected here has a refractive index of 1.5 and an edge width $l_k$ of, for example, 40 mm; an angular tolerance of ±5⁰ will therefore be used.

Each optical unit 31 or 32 has a ferrule 41a or 41b for gripping the end of the monomode fiber 25b or 26b averted from the polarization controller 27 or 29. Downstream of the ferrule 41a or 41b, the radiation guided in the monomode fiber 25b or 26b is propagated as a free space beam 42a or 42b and is collimated by means of a lens unit 43a or 43b to form the free space beam 33a or 35a. The lens unit 43a or 43b can now be an achromat, a single lens or else a lens system. The beam retroreflected by the respective mirror 37 or 39 is coupled into the monomode fiber 25b or 26b by the lens unit 43a or 43b via the ferrule 41a or 41b.

The path length variation element 23 as described, inter alia, in EP 0 877 913 is shown in different rotational angle positions in an enlarged illustration in FIGS. 2a to 2c. The following considerations relate to the reference arm 12 shown in FIG. 1 and to the free space beam 35a of said arm and the mirror 39, shown there, in the optical unit 32. The element 23 can be set rotating in accordance with the arrow 45 by a drive that is not illustrated. A cross sectional surface 46 of the element 23 that is shown in FIGS. 2a to 2c and lies at right angles to the element axis 21 and in which the second reference beam 35b, 35c and 35d in the element 23 comes to lie has four corners 47a to 47d with a corner angle γ of 90°, and is of square design in the example of the description selected here, that is to say the element 23 is a straight cylinder with a square base surface or cross sectional surface. The rotation axis 21 is identical to the axis of the cylinder. Each lateral cylinder surface 49a to 49d of the element 23 is provided with a partial coating 50a to 50d that is selected in such a way that it optimally reflects the component beam 35c located in the element 23, or the retroreflected component beam 35d of the reference beam of the second reference arm 12. No reflection coating is required at the reflection point 51 of the beam 35b or the retroreflected beam 35c at the wall 49b depicted here by way of example, since total reflection occurs here. The coatings 50a to 50d respectively begin at the corners (edges) 47a to 47d and extend over a distance a (FIG. 2a) into the relevant side face 49a to 49d. Starting from each corner 47a to 47d, respectively only one of the two adjoining sides is coated, specifically in each case only ever those on which the reflected beam forms an acute angle β with the incident beam, see FIG. 2c in particular to this end.

In the momentary position of the rotating element 23 illustrated in FIG. 2a, its side 49a is illustrated as being parallel to the surface of the mirror (reflector) 39. The reference beam 35a entering the element 23 is guided in such a way that it can be guided precisely past the right-hand edge 53 illustrated in FIGS. 2a, 2b and 2c, of the mirror 39. A distance e from the edge 53 of the mirror 39 (or 37) is selected to be precisely so large that it is only slightly smaller than half the cube edge width $l_k$. In the case of the reference example chosen here which has a face width $l_k$ of 30 mm, (by comparison with the abovementioned 40 mm), the reference beam 35a is irradiated at a distance e of 13 mm from the central rotation axis 21 and at a distance of approximately 1 mm from the right-hand edge 53 of the mirror 39 (or 37).

By comparison with the illustration in FIG. 2a, FIG. 2b shows the element 23 in a rotated by an exemplary angle α of 20°. Upon refraction, the beam 35a enters the transparent medium of the element 23 as beam 35b and is totally reflected at the surface 49b. The impinging and the reflected beam 35b and 35c form an obtuse angle with one another. The reflected beam 35c strikes the inside of the surface 50c and is reflected there by the coated region 50c as beam 35d in the direction of the surface 49a parallel to the beam 35b. The two beams 35c and 35d form an acute angle β with one another. The beam 35d impinging on the surface 49a is refracted, strikes the mirror 39 perpendicularly as beam 35e and is reflected back into itself again there with an approximately 100% reflection such that, after traversing the path length variation element 23, the beam reflected at the mirror 39 finally leaves said element in the same direction as the entering beam 35a. As may be seen from a comparison of FIGS. 2b and 2c, the reflection point 54 of the beam 35e moves to and fro on the mirror 39 (or 37).

The path length change Δs owing to the rotation of the element 23 is now composed of twice the path of the changing path lengths of the beams 35a to 35e. It is to be ensured for the beams 35b to 35d that their path lengths are extended by the refractive index n of the medium in which they run. In accordance with FIG. 2c, the path length change Δs is a function of the rotational angle α, the distance of the beam entry e, the refractive index n and the face width $l_k$ of the surfaces 49a to 49d. The calculation of the path length change Δs via the rotational angle α is derived in EP 0 877 913, and yields a substantially linear path length change over a rotational angle of 45°.

In order not to overload FIGS. 2a to 2c, only the free space beam 33a of the second reference arm 11 is illustrated. That is to say, the beam path of the beams 33a to 33d not depicted in detail corresponds to the beam path of the beams 35a to 35d at an identical impingement angle on the corresponding lateral cylinder surface 49a to 49d for the beam 33a. A beam path of the beams 33a to 33d in the position of the element 23 shown in FIG. 2a is to be equated to the beam path of the beams 35a to 35d in FIG. 2c. It results after a rotation by half the corner angle γ/2; the corresponding component beams are therefore placed in round brackets. The beam path of the beams 35a to 35d in FIG. 2c would then correspond to a beam path of the beams 33a to 33d in FIG. 2a. A beam 33a impinging at the element position shown in FIG. 2b is no longer reflected back to the corresponding mirror 37.

The data specified above relate to a material of the path length variation element that has a refractive index of approximately 1.5 in the case of the radiation of the radiation source. If a material of higher refractive index is used, the coating width a of the reflecting coatings 50a to 50d can be reduced so that the temporal measuring ranges of the reference arms can be kept apart.

The optical lengths of the reference arms 11 and 12 can be designed so as thereby not to cause the two measuring ranges made available by the reference arms 11 and 12 to be joined seamlessly to one another in a space. If the reference arm responsible for the rear eye section is designed to be long enough, the measuring range of the reference arm responsible for the rear eye section thus begins at a position that lies closer to the retina by a prescribed path length than the position, lying deepest in the eye 19, of the reference arm responsible for the front eye section. This measure results in a scan gap between the front and the rear depth scan. That is to say, there is a prescribed distance (that can be set by design) between a front eye section and a rear eye section on which no reflective structures can be measured.

In the case of the human eye, this scan gap will be selected with the order of magnitude of approximately 4 mm to 10 mm. When recording the depth scan of the cornea over the crystalline lens up to the retina, such a scan gap leads to a negligibly minimal loss of information, because this scan gap has been placed in an eye region in which no eye structure to be measured is present for an overwhelming number of patients or normal subjects; the scan gap is placed behind the lens surface in the foremost part of the vitreous body. An advantage of the scan gap consists in that the path length variation element 23 rotating about an axis must make available a scanning depth that is shorter by the path length corresponding to the scan gap. It is therefore possible to use a path length variation element 23 with a shorter side length 49a to 49d, and this entails a higher sensitivity in conjunction with the same scanning speed.

The polarization controllers 18, 27 and 29 arranged in the two reference arms 11 and 12 and in the measurement arm 13 serve the purpose of adapting the radiation polarizations in the arms 11, 12 and 13. The optical path length differences of the two reference arms 11 and 12 are always set such that the difference between the fundamental delay times of the two reference arms 11 and 12 corresponds to half the maximum lengths to be measured, here the eye length, for example.

If the differences between the two reference arms are greater, it is also possible to measure longer distances, but with the restriction that reflections in a region lying therebetween cannot be detected.

Seen in terms of time, the two interferences occur very quickly after one another in accordance with the speed of rotation and the number of lateral cylinder surfaces of the path length variation element 23. Since in the case of distances, thickness measurements, . . . it has always been necessary in the prior art to undertake two measurements staggered in time, in the case of the invention the measurement result is now quickly to hand in such a way that spatial displacements of the object to be measured influence the measuring accuracy only insubstantially. The advantage just outlined is of substantial use in the case of length measurement on the eyes of children, who can generally be kept still only with difficulty.

The measuring head 20 not described in great detail in FIG. 1 is shown in more detail in FIG. 3. The monomode fiber 14b of the measurement arm 13 enters the measuring head 20. A so-called ferrule 57 is arranged for holding purposes at the end of the fiber 14b. The radiation guided into the fiber 14b exits from the ferrule 57 in accordance with the fiber core at a prescribed aperture angle, and is focused with the aid of a focusing unit 58 that has a lens unit 59 onto a front surface of a layer whose thickness is to be determined. In the example selected here, a layer can be provided as the cornea of the eye (measurement object 19). As already mentioned above, it is advantageous in the case of determining layer thickness when the measurement radiation can be focused both on the front side and, subsequently, on the rear side. If it is now the aim to focus on the rear side of the layer, a plane parallel plate 61 with a prescribed refractive index n and prescribed thickness d is pushed in as part of the focusing unit 58 between the ferrule 57 and the lens unit 59. This plate 61 produces an image offset v of the fiber end in the ferrule 57, and thus also a displacement of the focal point in the depth of the object. In conjunction with the optical imaging data of the lens unit 59, the image offset is now selected by a suitable selection of the thickness d and the refractive index n of the plane parallel plate 61 in such a way that the fiber end in the ferrule 57 is imaged on the rear side of the layer, that is to say here on the retina (rear side of the eye). Introducing the plate 61 into the measuring beam 22 is undertaken synchronously with the above-described path variation element 23 in such a way that a path length variation is performed precisely by means of that reference arm which is responsible for determining the front side of the layer (→no plate, that is to say plate withdrawn) or for the rear side of the layer (→plate pushed in).

Since there are now a few difficulties in pushing a plane parallel plate 61 to and fro, it is proposed instead of this to use a rotating disk 63, illustrated in FIG. 4, with projecting edge segments 64 of a circular ring ("toothing"), whose disk sides are of plane parallel and transparent design. During measurement of the front side of the layer, the measurement radiation emanating from the ferrule 57 now traverses one of the interspaces 65 between the edge segments 64 of the circular ring, and it traverses one of the segments 64 of the circular ring during measurement of the rear side of the layer. The rotary movement of the disk 63 is coupled to the rotation of the path length variation element 23 via a drive (not illustrated).

As already mentioned at the beginning it is advantageous when the topography as further geometric value of the relevant layer can also be determined, in addition to determining layer thicknesses, in particular in the case of the human eye. As likewise shown in FIG. 3, the measuring head 20 can include additional components for the purpose of determining the topography of surfaces.

An optical structural unit 70 with regions of different luminance is arranged upstream of the surface whose topography, here the cornea 69, is to be determined. The reflections of this structure on the cornea are imaged, and this image is evaluated. Since the geometry of the structure is known, it is possible, as stated in the introduction, to infer the surface topography from the geometry in the image.

The measuring beam 22 for determining layer thickness is preferably guided in the middle through the structural unit 70. To this end, the beam 22 is deflected downstream of the lens unit 59 with the aid of a mirror 71 operating in a wavelength-selective fashion. So that this mirror 71 can act, different wavelengths are used for the measurement radiation in relation to the determination of layer thickness, and for the radiation of the structure. The mirror 71 therefore has a coating that reflects the measurement radiation but transmits the "structural radiation" (approximately) without loss. In a rearward extension, the beam 22 defines an optical axis 68 for imaging the reflecting structures on the corneal surface 69.

In order to image the structure reflected by the corneal surface 69, use is made of a further lens unit 72 with downstream diaphragm that images the corneal surface 69 onto the image plane of a camera chip 73. The lens system 72 is arranged between the mirror 71 and the camera chip 73. A blocking filter 75 for the measurement radiation is arranged between the mirror 71 and the camera chip 73 so that the measurement radiation of the beam 22 does not interfere with the topography evaluation. The measurement radiation can simultaneously be used for the patient as fixation radiation for steadying the eye. The camera chip 73 is connected to an evaluation unit 74 that, in addition, also is connected to the detection unit 17. The evaluation unit 74 is part of the apparatus already described above and further below, and serves for processing, transmitting and displaying all the measured data.

Figure 6:
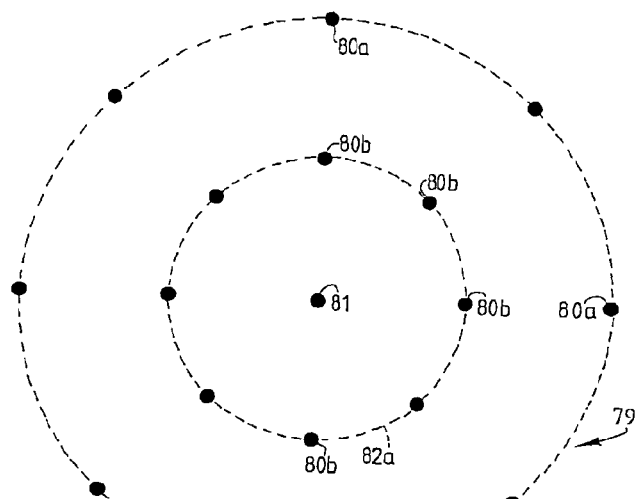
FIG. 6 shows a plan view of an optical structural unit of the measuring head illustrated in FIG. 3.

An exemplary design 79 of an optical structural unit 70 is illustrated in FIG. 6. The structural unit 79 has 16 LEDs 80a and 80b, which are arranged in two concentric rings 82a and 82b of eight LEDs each. The angular difference between two consecutive LEDS is 45°. These LEDs preferably radiate in the invisible, or scarcely visible infrared region. In this case, the patient's eye is not deflected by unnecessary light stimuli. It is also possible to use more than two rings and also more than eight LEDs per ring.

Two LEDs whose geometric connecting line passes through the center 81 of the structural unit permit the measurement of a mean radius of curvature between the connecting line of the two LED images (=measurement of a corneal meridian). When adapting the refractive power of an intraocular lens, it is chiefly the steepest and the flattest meridian, or the mean value of the two, that are of interest from the multiplicity of corneal radii of curvature of the meridians. The directions of the steepest and the flattest meridian need not necessarily correspond to the direction of one of the measured radii of curvature. The flattest radius of curvature can also further be a little flatter than the greatest of the measured radii of curvature, and the steepest radius of curvature can also further be a little smaller than the steepest of the measured radii of curvature.

At least five LEDs must be to hand so that the steepest and the flattest meridian and the axial angle of the flat meridian can be calculated. All the LEDs are simultaneously switched on and off when measuring the radii of curvature.

A mean radius of curvature can be calculated between two arbitrary LEDs whose connecting line need not necessarily pass through the center 81. This mean radius of curvature strikes the connecting line between the two corresponding LEDs. The number of the measurable radii of curvature per surface unit increases with the number of LEDs to hand. A corneal topography can be calculated given a sufficiently large number of LEDs. The greater the number of measuring points (=LEDs), the more accurately a topography can be determined. An arbitrary number of concentric rings, and an arbitrary number of LEDs per ring can be used for measuring the corneal radii. Again, an arbitrary number of concentric rings and an arbitrary number of LEDs per ring can be used as fixation emitters. The number of the LEDs used is bounded above only by the diameter of the ring and the dimensions of the LEDs.

The measuring beam 22 of the interferometer arrangement can also be used for distance measurement between the apparatus and the front corneal surface as measurement object 19. This distance is required when the distances between the various LED spots imaged on the camera chip 73 are a function of the distance between the LEDs and the front corneal surface to be measured. This dependence on distance emerges substantially chiefly when no telecentric lens is used for the lens unit 72, for example for reasons of costs. The distance measurement then permits for an exact calculation of the corneal radii of curvature than would be possible without knowledge of distances. The distance to be measured to the front corneal surface is determined by using either the reference arm 11 or the reference arm 12.

Since a packing density of LEDs is limited, (each individual LED has a prescribed geometric extent), it is possible to use a pinhole diaphragm that is irradiated from the rear by a number of LEDs. The diameter of the holes of the pinhole diaphragm can be selected to be substantially smaller than the extent of each LED. A greater number of luminous points can thereby be obtained. The pinhole diaphragm need not necessarily have circular holes—lines could also be present. These lines can be designed as concentric circles and as a combination of concentric circles and beams cutting the latter.

As is indicated in FIG. 3, it is also possible to place a diffusing screen 83 upstream of the LEDs. The diffusing screen 83 produces on the surface to be measured a luminance spot whose lateral extent results from the LED emission angle, the thickness of the diffusing screen and the distance between the diffusing screen 83 and the relevant LED. The diffusing screen 83 is not mandatory. If no diffusing screen 83 is present, the LED imaged on the camera chip has a smaller diameter. A disadvantage of excessively small imaged diameters may be, inter alia, reduced accuracy of the determination of a centroid of the imaged spot. A spot having only a few pixels can generally be measured less accurately than a spot having a larger number of pixels. If a diffusing screen 83 is used, LEDs of higher luminance can be used, since the strength of irradiation on the eye is then lower.

Figure 7:
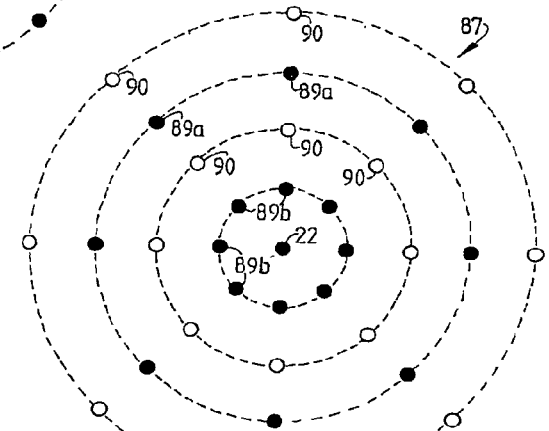
FIG. 7 shows a plan view of a variant of an optical structural unit that can be used to determine peripheral, intraocular distances, lengths or thicknesses.

LEDs 80a and 80b emitting invisible or scarcely visible radiation were used in the case of the structural unit 79 shown in FIG. 6. FIG. 7 now illustrates an optical structural unit 87 in the case of which there are arranged between radially arranged LEDs 89a and 89b that preferably shine in infrared further LEDS 90 that shine in the visible. If one of these LEDs 90 is now switched on, the patient is offered a peripheral fixation point. If the patient now fixates on this light stimulus, he moves the axis of the eye onto this point, it then being possible to use the measuring beam 22 for an interferometric measurement of peripheral intraocular distances, lengths or thicknesses. By contrast with known apparatuses, there is no need to undertake to swing the arrangement.

Figure 12A:
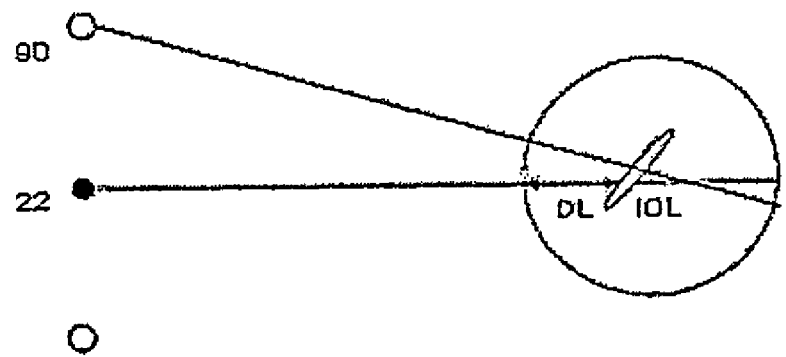
FIGS. 12a-b show a schematic of the measurement of the position of an IOL.
Figure 12B:
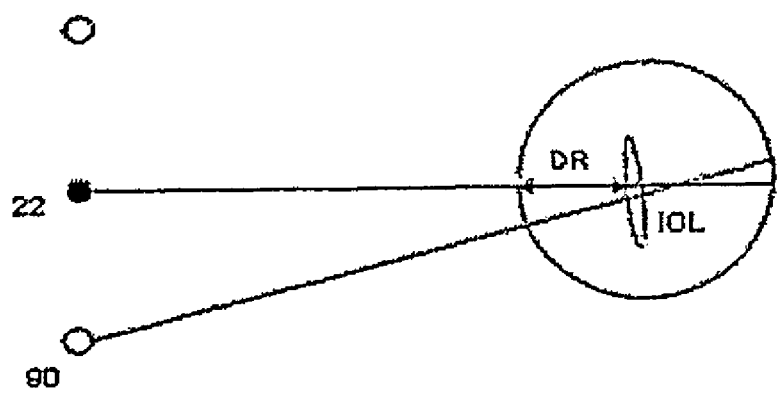

If four peripheral measurements with the measuring beam 22 are carried out consecutively with the aid of four different visible LEDs 90 (fixation LEDs) switched on consecutively over time, it is possible therefrom to measure the tilting of an implanted intraocular lens (IOL). FIG. 12 shows only the measurement of the horizontal tilt with the aid of two horizontal LEDs 90 switched on consecutively over time. If it emerges as a result of the two measurements shown that the distance DL ("distance to the left") is not equal to the distance DR ("distance to the right"), the IOL is thus horizontally tilted. Two vertical LEDs 90 must be switched on consecutively over time in order to measure the vertical tilting. Knowledge of the tilting provides the doctor with a basis for decision in order to realign a tilted intraocular lens.

Figure 8:
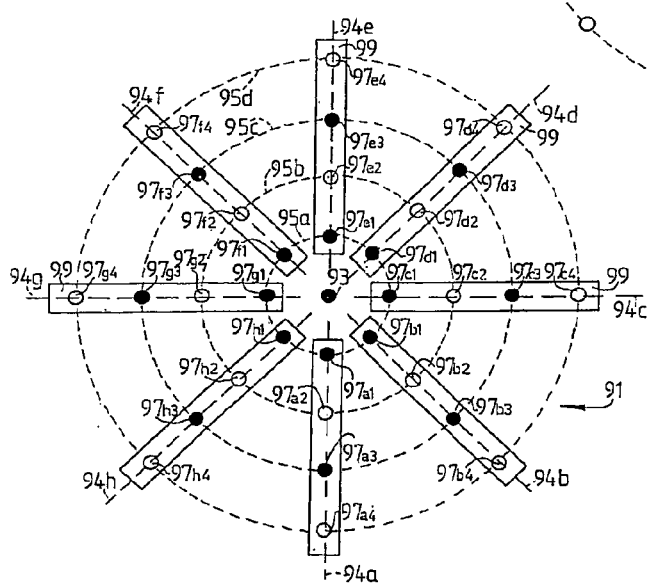
FIG. 8 shows a plan view of a further variant of an optical structural unit.

FIG. 8 illustrates a further variant embodiment 91 relating to the optical structural units 70 and 87. This structural unit 91 can be used not only to measure the front corneal surface, but also to measure the rear corneal surface, as well as the front surface of the lens and the rear surface of the lens. In the example shown here, four LEDs 97 arranged on coaxial circles 95a to 95d are respectively present in an arrangement of eight branches 94a to 94h that is in the shape of a radial star relative to a center 93. The LEDs of a branch 94a to 94h are respectively additionally marked with the letters of the branch in a fashion running from inside to outside. An LED lying innermost in the branch 94a therefore has the designation $94a_1$, and an LED lying outermost the designation $97a_4$. A cylindrical lens 99 is respectively arranged above each of the branches 94a to 94h. The eight cylindrical lenses 99 focus the LEDs 97 onto a region between the cornea and crystalline lens. If there is now switched on a row of LEDs, for example the LEDs $97a_4$ to $97a_1$ and $97e_1$ to $97e_4$, that lie on a connecting line cutting the center 93, a light gap is produced on the eye. The LEDs $97a_4$ to $97a_1$ and $97e_1$ to $97e_4$ are then switched off with a short time delay, and the LEDs $97b_4$ to $97b_1$ and $97f_1$ to $97f_4$ are then switched on. Subsequently, the LEDs $94b_4$ to $97b_1$ and $97f_1$ to $97f_4$ are switched off, and the LEDs $97c_4$ to $97c_1$ and $97g_1$ to $97g_4$ are switched on, etc. This produces a light gap rotating about the center 93. A camera arranged centrally in a fashion analogous to that in FIG. 3 then views a sequence of light gaps that are projected into the eye by the cylindrical lenses 99. Two peripherally arranged cameras (not illustrated) (for example, one vertically, one horizontally arranged) permits additional measurement of the light gaps. The topography of the rear corneal surface, the anterior chamber depth (in three dimension), the topography of the lens front surface and of the lens rear surface, the lens thickness, (in three dimensions) and the phacoscotasmus can be calculated from the positions of the light gaps appearing on the camera chip. The above-described interferometer arrangement (see FIG. 3) is used in order to determine the distance that there was during the production of the camera images. The surfaces then measured by the camera are further corrected with the aid of the measured distance.

By contrast with the illustration in FIG. 8, it is also possible to use another number of LEDs. A preferably linearly operating diffuser (not illustrated) can additionally be arranged between the LEDs and the cylindrical lenses in order to let the light spots of the punctiform LEDs flow into one another. It is possible thereby to produce homogenously illuminated light gaps.

Instead of switching the LEDs on and off consecutively, it is also possible to move a rotating mechanical gap over all the switched on LEDs.

Instead of the eight cylindrical lenses 99 shown in FIG. 8, it is also possible to use only one pair of cylindrical lenses (not illustrated) having two mutually aligned cylindrical lenses and which rotates about the center 93.

The rotating disk 63 illustrated in FIG. 4 and having fragments of a circular ring serves a purpose of switching over the focusing of the measurement radiation onto two different focal points. If the aim is now to switch over onto more than two focal points, the segments would need to have a corresponding number of plane parallel steppings, depending on the number of focal points to be switched over. Such a stepping can be produced only with difficulty and a large outlay. In order to obtain such a stepping, a number of plane parallel disks 131 and 132 provided with corresponding cutouts resembling segments of a circular ring will therefore be laid on one another to form a focal point displacement device 130 as illustrated in FIGS. 5a to 5d. The disk 131 sketched in FIG. 5a now corresponds, for example, in its contour to the rotating, plane parallel disk 63 shown in FIG. 4, in which case the thickness could differ. In the case of an eye examination, for example, the purpose of the disk 131 during the operation of the reference arm 11, for example, is to displace the focus from the corneal surface to the retina, said disk having the thickness $b_1$. The cornea would always be focused on whenever the measuring beam passes through the free segments 133 of a circular ring, and the retina would be focused on when the beam passes through the transparent material of the edge segments 135 of a circular ring. What has been said above is valid if the distance between the ferrule 57 and lens 59 in FIG. 3 is greater than the focal length of the lens. In the reverse case, that is to say given a distance of the ferrule 57 that is smaller than the focal length of the lens, the retina is measured when the measuring beam passes through the free edge segment of a circular ring. The cornea is measured when the beam passes through the transparent edge segment of a circular ring. Since, particularly in the case of cataract patients, the retina signal is weaker than in the case of a normal retina, the last named design is preferably used with cataract patients.

There are four segments 133 and 135 of a circular ring present in each case, these being arranged in an alternating fashion. A central angle φ of each segment 133 or 135 of a circular ring is 45°. The outer circular arc of the segment 133 of a circular ring has a radius $r_1$, and the segment 135 of a circular ring has an outer circular arc, increased by Δr, with a radius $r_2$. Δr is selected to be so large that the measuring beam 22 has enough room. There are thus always two identical segments 133 and 135 of a circular ring lying diagonally opposite one another.

Figure 5A:
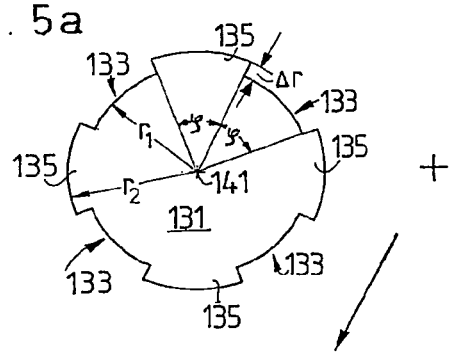
FIG. 5a shows a plan view of one disk.
Figure 5B:
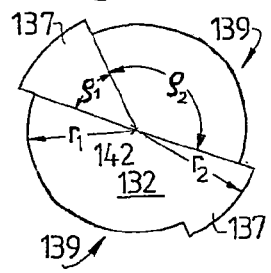
FIG. 5b shows a plan view of the other disk.

The second disk 132, sketched in FIG. 5b, then has the task while the reference arm 12 is in action of placing the focal point in the crystalline lens, and has the thickness $b_2$. The thickness $b_2$ of the rotating plane parallel disk 132 differs from the thickness $b_1$ of the disk 131. The disk 132 has two edge segments 137, of transparent material, of a circular ring that are diagonally opposite one another and respectively have a central angle $p_1$ of 45° and a radius $r_2$. The two free pieces 139 of a circular ring lying between the segments 137 of a circular ring therefore have a central angle $p_2$ of 135° and a radius $r_1$.

Figure 5C:
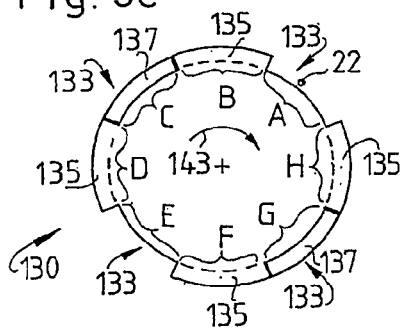
FIG. 5c shows a plan view of the focal point displacement unit consisting of two disks.
Figure 5D:
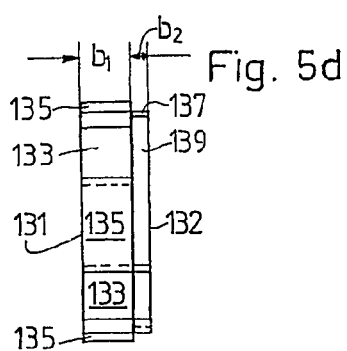
FIG. 5d shows a side view of the unit illustrated in FIG. 5c.

As indicated in FIG. 5c, the two disks 131 and 132 are placed one above another in such a way that, on the one hand, their rotation axes 141 and 142 are aligned and, on the other hand, the segments 137, of transparent material, of a circular ring respectively come to lie behind two of the four free segments 133 of a circular ring.

In FIG. 5c the measuring beam 22 is located precisely in the free segments 133 and 137 of a circular ring (region A), the result being that the cornea is focused on in the above example of an eye examination. If the focal point displacement device 130 of the focusing unit 58 is rotated further in the direction of the rotation arrow 143 in FIG. 5c, then the measuring beam 22 passes the edge segment 135, of transparent material, of a circular ring, which segment has the large thickness $b_1$ (region B), the result being to focus onto the retina. After a further rotation, the measuring beam 22 passes through the edge segment 137, of transparent material, of a circular ring with the thin thickness $b_2$ (region C), as a result of which the focus is placed in the crystalline lens and the thickness thereof is determined. If there is further rotation to the region D, the measuring beam 22 again passes through material with the thickness $b_1$, and the retina is therefore focused on in a fashion similar to region B. In the region E the measuring beam 22 passes only through air, and is therefore focused onto the cornea. In the region F, focusing is once again onto the retina, while in the region G the thickness of the crystalline lens is measured and in region H the retina is once again focused on. The arrangement described here can therefore be used to determine the eye length and the thickness of the crystalline lens in one measuring method.

The focal point displacement device 130 outlined above operates with two rotating disks that have free arc pieces. The respective position of the focal point is determined by the respective thickness of the material currently being passed through, and by the refractive index thereof. A focal point displacement device can now also be designed in such a way that the thicknesses of the individual disks add up to form a total thickness. However, it must then also be ensured that no air gaps that would cause undesirable reflections are produced between the plates. However, instead of two disks it is also possible to use more. Again, it is possible to undertake a greater subdivision such that further focal points are produced instead of the three focal points outlined above.

Of course, it is also possible to use three, four and more reference arms at appropriate mutual angles instead of just the two reference arms 11 and 12. The individual reference arms can also be connected and disconnected with the aid of appropriate beam interrupters, synchronized with the rotation of the path variation element, upstream of the single path variation element.

Instead of the path length variation element 23 described in EP 0 877 913 and illustrated in FIGS. 1, 2a, 2b and 2c, it is also possible to make use, with a few changes, of the path length variation elements illustrated in FIGS. 1 to 3 of DE 34 46 014. During use of the path length variation element 23, the latter is transirradiated by the reference beams. By contrast, in the case of the path length variation element 103 illustrated in FIG. 9 the reference beams are reflected at its surface; the reference beams do not enter the path length variation element 103. The path length variation element 103 is likewise designed as a body rotating about an axis 105. Six isosceles roof prisms 107a to 107f with silvered external faces 109a to 109l are arranged on a straight circular cylinder 106. External faces 109a/109l, 109c/109b, 109e/109d, 109g/109f, 109i/109h and 109k/109j meeting at the base of the roof prisms 107a to 107f on the circular cylinder 106 respectively enclose a right angle ϵ with one another. A free beam 111a of a reference arm 112 designed by analogy with the reference arm 12 is guided through an opening 113, there being arranged in FIG. 9 above the opening 113 a mirror 115 that runs perpendicular to the beam 111a and is designed to reflect approximately 100% of the radiation of the beam 111a. An absorber 116 for the radiation of the beam 111a is arranged under the opening 113. In the position, illustrated in FIG. 9, of the path length variation element 103, the beam 111a now strikes the external face 109a and is reflected from here as beam 111b to the external face 109l, and is guided thereby onto the mirror 115 in a fashion parallel to the beam 111a as beam 111c and retroreflected into itself such that it passes again, as reflected beam, through the opening 113. Because of the right angle ϵ, the beam impinging on the mirror 115 is always retroreflected into itself even when the path length variation element 103 has been rotated further by an angle in the direction of the arrow 118, as indicated by dashes in FIG. 9. The impingement point 117 of the beam 111c moves away from the opening 113 in FIG. 9 upward until the beam 111a falls onto the tip 119a of the roof prism 107a. If the path length variation element 103 is rotated further, the beam 111c strikes the absorber 116 in a fashion remote from the opening 113, and then moves in the direction of the opening 113; that is to say there is now no reflection of the beam.

Figure 9:
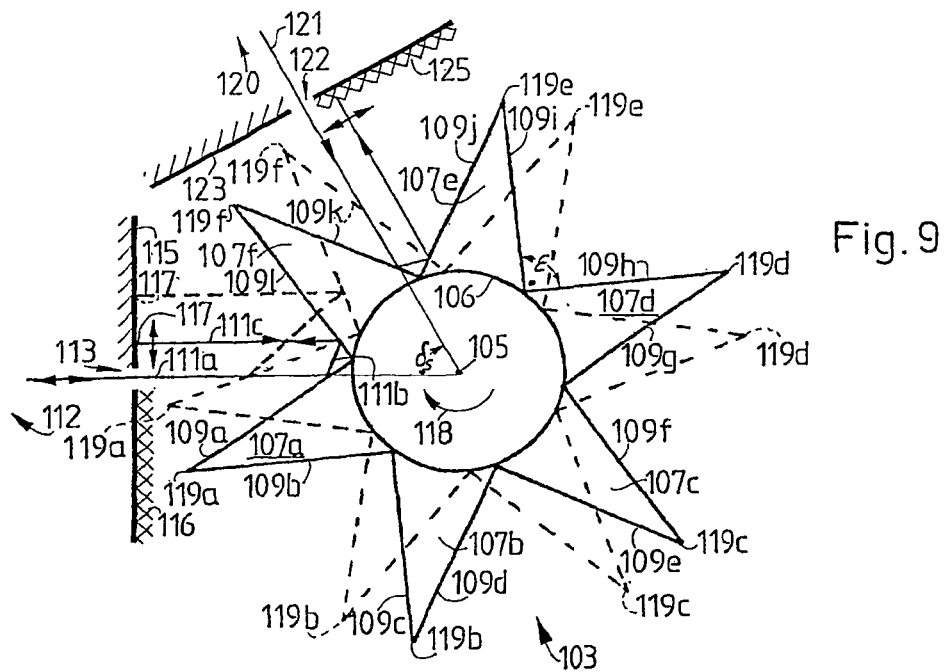
FIG. 9 shows a schematic of a variant of the path length variation element illustrated in FIGS. 1, 2a, 2b and 2c.

A beam 121 of a second reference arm 120, designed by analogy with the reference arm 11, passes through an opening 122 and strikes a tip 119f of the roof prism 107f at the instant when the beam 111a strikes the tip 119a, and, after a short further rotation of the face 109l, is reflected onto the face 109a and thereby onto a mirror 123, and reflected back into itself again from there such that the reflected beam passes again through the opening 122. If the path length variation element 103 has been further rotated so far that the beam 121 strikes the face 109a, the beam then reflected at the face 109l falls again onto an absorber 125 as illustrated in FIG. 9, obliquely above the opening 122. The two incident beams 111a and 121 enclose an offset angle $\delta_s$ with one another. Except for for a tolerance, the offset angle $\delta_s$ corresponds to the central angle of respectively neighboring tips of the roof prisms. The greater the tolerance is selected here, as well, the smaller is the path length variation.

When the beam 111c strikes the reflector 115, the beam 121 deflected by reflections strikes the absorber 125. If the reflected beam 119 strikes the mirror 123, the beam 111c strikes the absorber 116.

Instead of designing the path length variation element 103 with six roof prisms 107a to 107f, it is also possible to use another number of roof prisms: however, neighboring faces must always meet at an angle of 90° on the circular cylinder.

Figure 10:
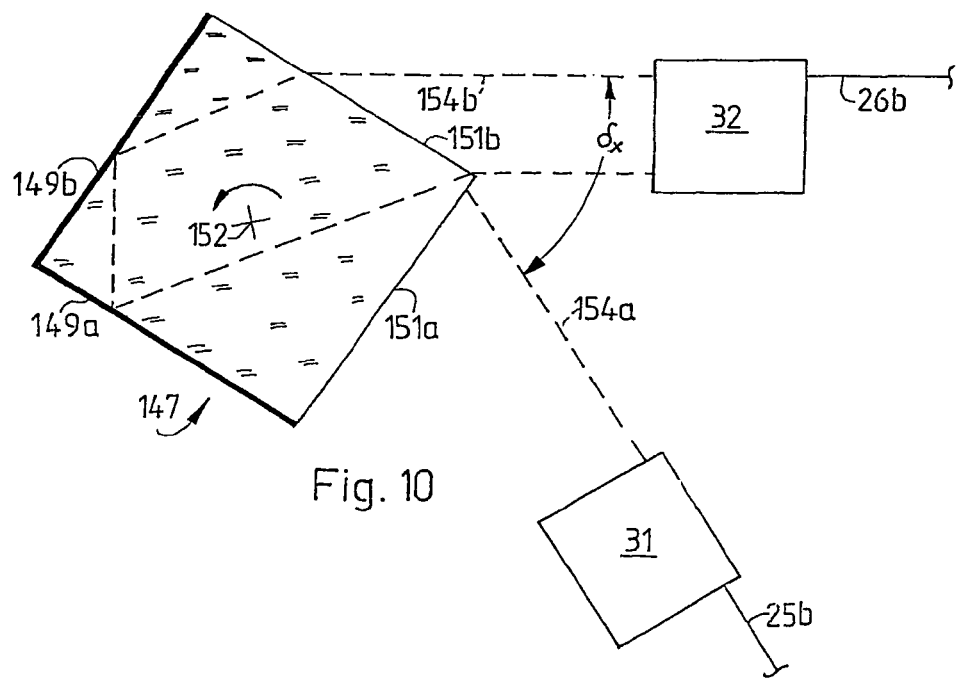
FIG. 10 shows a further variant of the path length variation element illustrated in FIGS. 1, 2a, 2b and 2c.

The path length variation element 23 described in EP 0 877 913 is illustrated in FIGS. 2a to 2c, and in this case the lateral cylinder surfaces 49a to 49d emanating from the corners 47a to 47d have only a coating 50a to 50d that is partially approximately 100%. In the case of a variant of a path length variation element 147 illustrated in FIG. 10, which likewise has a square cross section, two neighboring lateral cylinder surfaces 149a and 149b are provided completely with an approximately 100% reflecting coating, and the other two lateral cylinder surfaces 151a and 151b are provided without a reflecting coating, preferably with an antireflecting coating. The path length variation element 147 likewise rotates about a rotation axis 152. Given a refractive index of n=1.5 for the material of the path length variation element 147, rotation of 0° to 58° is possible without stopping the path length variation. This increases the maximum possible scanning depth for a lateral cylinder surface by comparison with the path length variation element 23, illustrated in FIGS. 2a to 2c, in one reference arm in each case. (Only a maximum rotary movement by 44° is possible in the case of the path length variation element 23.) By comparison with an only partial reflective coating (path length variation element 23), it is disadvantageous in the case of a reflective coating that covers the entire side length (path length variation element 23) that measurement can be performed per reference arm only twice instead of four times per rotation. In order for no interfering temporal overlaps to be produced during the scanning time of the two reference arms in the case of a complete lateral coating, the angle $\delta_x$ between the two beams 154a and 154b, striking the path length variation element 147, of the two reference arms must not be 45°, but at least 58°.

Figure 11:
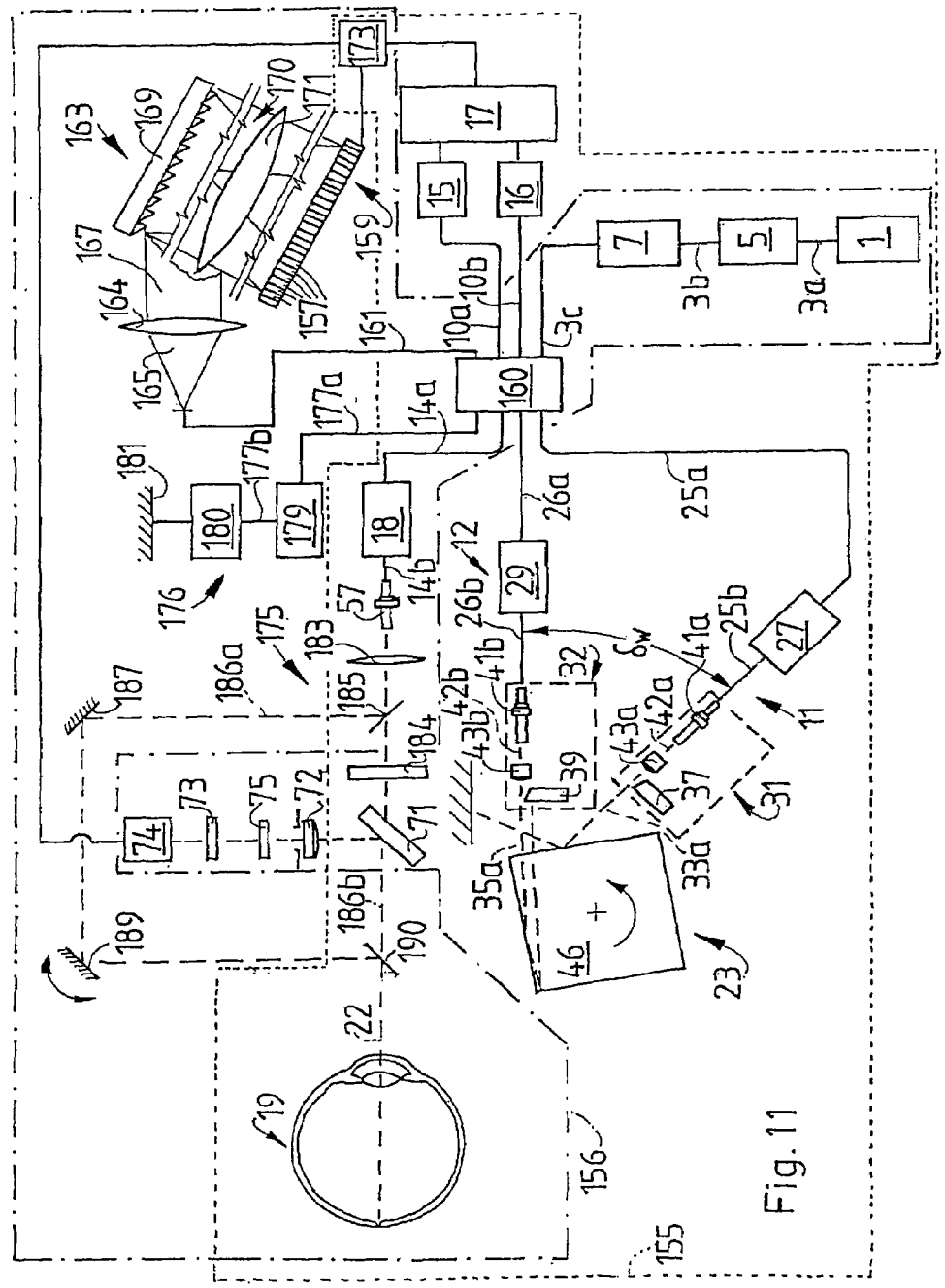
FIG. 11 shows a variant of the apparatus illustrated in FIG. 1, in the case of which it is possible, in addition to determining thicknesses and/or path lengths with the aid of a time domain optical coherence tomograph, to determine a topography, a two- or one-dimensional tomography, with the aid of a spectral domain optical tomograph.

FIG. 11 illustrates an apparatus for determining at least one geometric value on transparent or diffusive objects with the aid of a time domain optical coherence tomograph (TDOCT) 155 and a spectral domain optical coherence tomograph (SDOCT) 156. The components of the TDOCT 155 are surrounded with a dotted line, and those of the SDOCT 156 are surrounded with a dashed and dotted line. The TDOCT 155 essentially includes the components illustrated in FIG. 1. By connecting the TDOCT 155 to an SDOCT 156, it is now possible to combine the advantages of these two tomographs with one another. In addition to a determination of a thickness, a distance and/or a length, it is now also possible to determine a topography quickly and accurately. This combined measurement is certainly also possible with the aid of the above-described apparatus illustrated in FIG. 1 with an appropriately designed measuring head 20 as described above, but the use of an SDOCT 156 instead of the above-described LED arrangements yields tomograph data that can be determined more exactly and more quickly, it being possible in addition to determine topographies in the interior of the object.

An SDOCT 156 alone is described, for example, in the publication by R. A. Leitgeb, W. Drexler, A. Untergrube, B. Hermann, T. Bajraszewski, T. Ie, A. Stingl, A. F. Fercher, "Ultrahigh Resolution Fourier Domain Optical Coherence Tomography, Optics Express, Vol. 12, No. 10, 17 May 2004, pages 2156-2165 and is used there not to determine a topography but to determine layer thicknesses.

In the case of an exemplary use on the eye, the SDOCT 156 measures either the front eye segment or the rear eye segment because, by contrast with the TDOCT 155, in the case of the SDOCT 156 the maximum possible scanning depth is typically restricted to a few millimeters. One reason for this restriction is to be sought in the number of available camera pixels 157 that are present in a camera line 159; each line 159 typically has 1000 pixels. By contrast with the SDOCT 156, the TDOCT 155 is capable of measuring lengths of typically 30 mm to 40 mm. However, the measurement sensitivity and the scanning speed of the SDOCT 156 are greater by a few factors than those of the TDOCT 155. Because of the higher sensitivity and the higher speed, the SDOCT 156 is used in the measurement object to scan a surface (two dimensionally) or a volume (three dimensionally) with a depth of typically 3 mm, depending on how a mirror 189 described below reflects the measuring beam 186a into one or two directions. By contrast with the SDOCT 156, the TDOCT 155 measures only in one dimension in the measurement object.

The TDOCT 155 illustrated in FIG. 11 essentially has the components already shown in FIG. 1, with the extent that the components identical to those in FIG. 1 have the same reference symbols. Thus, by analogy with FIG. 1 there are present a radiation source 1, a radiation attenuator 5, a polarization controller 7 and analogously designed reference arms 11 and 12 with a path length variation element 23, it also being possible to design the path length variation element 23 as path length variation element 103 or 147. Furthermore, as illustrated in FIG. 1 the TDOCT 155 has the two detectors 15 and 16 and the detection electronics 17. The measuring head 20 present in FIG. 1 and the monomode fiber coupler 9 are, however, of different design and are described below.

In addition to the components already specified above, the arrangement shown in FIG. 11 has a 4×4 monomode fiber coupler 160 that is connected on its right-hand side in FIG. 11 to the radiation conductors 3c, 10b, 10a and to a radiation conductor 161 that leads to a spectrometer 163.

The spectrometer 163 has a lens 164 that collimates the radiation 165 exiting from the radiation conductor 161. The collimated radiation 167 is guided to a grating 169. The grating 169 reflects into another direction each wavelength that is contained in the radiation 167 impinging the grating 169. This radiation 170 decomposed in terms of wavelength components is focused onto the camera line 159 having the camera pixels 157 by means of a focusing line 171. Each pixel 157 therefore always receives only a very specifically determined wavelength region. The positions of the various reflections occurring in the object 19, and thus a topography and/or a meridian can be determined by determining the intensities of the wavelength regions detected by the camera pixels, and with the aid of a mathematical conversion (Fourier transformation) in an evaluation unit 173.

On the left-hand side in FIG. 11, the 4×4 monomode fiber coupler 160 is connected to the two reference arms 11 and 12, a measurement arm 175 that differs from the measurement arm 13, and a further reference arm 176. The reference arm 176 is connected to the coupler 160 via a monomode fiber 177a. The other end of the monomode fiber 177a is connected to an optional phase modulator 179 that operates in a piezoelectric fashion, for example, and is connected to an optional polarization controller 180 via a monomode fiber 177b. Emanating from the polarization controller 180 the radiation reaches a mirror 181 by which the radiation is reflected back again to the coupler 160 via the components previously specified.

The measurement arm 175 connected to the coupler 160 has the polarization controller 18 illustrated in FIG. 1, and the ferrule 57 for the purpose of generating free space radiation. As described above, a focal point adjustment can be undertaken in a fashion synchronized with the path length measurement in the reference arms 11 and 12 with the aid of a lens and an optical element 184 designed by analogy with the optical elements 61, 63 or 130. A splitter mirror 185 is arranged between the lens 183 and the optical element 184. The radiation 186a coupled out with the aid of the splitter mirror 185 is guided via a deflecting mirror 187 onto a swinging mirror 189 and then onto a further splitter mirror 190. The radiation 186b not coupled out by the splitter mirror 185 is combined on the splitter mirror 190 with the radiation 186a deflected via the mirrors 187 and 189. The component beam 186a, which is part of the optical spectral domain tomograph 156, is deflected laterally over the eye segment to be measured, for example the front or rear one, by the movement of the swinging mirror 189.

In the fiber coupler 160, the radiation reflected by the reference arm 176 is superposed on the radiation retroreflected by the object 19. 25% of the radiation then goes from the fiber coupler 160 into the radiation conductor 161.

The TDOCT 155 thus includes as main components the path length variation element 23, the two reference arms 11 and 12, the 4×4 monomode fiber coupler 160, the radiation source 1, the radiation attenuator 5, the polarization controller 7, the two detectors 15 and 16, the detection electronics 17, the evaluation unit 173, the polarization controller 18, the ferrule 57, the lens 183, the optical unit 184 and the object (eye) 19.

The SDOCT 156 includes the radiation source 1, the radiation attenuator 5, the polarization controller 7, the 4×4 monomode fiber coupler 160, the spectrometer 163, the reference arm 176, the polarization controller 18, the ferrule 57, the lens 183, the splitter mirror 185, the deflecting mirror 187, the swinging mirror 189, the splitter mirror 190 and the object 19. In an advantageous refinement, there will be arranged between the swinging mirror 189 and the deflecting mirror 187 or the splitter mirror 185 a lens (not illustrated in FIG. 11), with the aid of which it is possible to focus the radiation onto the zone in the object 19 whose "internal" topography is to be determined, it also being possible, of course, to determine an "external" topography. However, this lens will not be arranged between the swinging mirror 189 and the splitter mirror 190, since then the beam would move on the lens surface as a consequence of the deflection of the swinging mirror.

The arrangement illustrated in FIG. 11 can additionally include the components shown in FIG. 3 for determining topography. In order not to overload FIG. 11, it is only the wavelength-selective mirror 71, the lens unit 72, the blocking filter 75 and the camera chip 73 that are drawn in. The LED arrangements are, of course, also present but are not drawn in. The arrangement analogous to FIG. 3 can be used to determine the topography of free surfaces, while the SDOCT 156 can also be used to determine topographies lying in the depth of the object in addition to free surfaces.

A number of eye structures can be measured in a single positioning aperation using the apparatuses described above. In addition to the respective topographies of surfaces lying outside or inside, it is thus possible in the case of the eye, for example, to determine the thickness and the internal structure of the cornea, of the anterior chamber, of the crystalline lens and of the vitreous body. In addition, it is further possible by means of a single positioning operation of the apparatus undertaken on the patient's eye to determine the lens cortex and phacoscotasmus, the eye length, the internal structure of the retina, the position and the thickness of phacic and pseudophacic intraocular lenses, the position and the thickness of contact lenses and the radius of curvature of the cornea, and to measure the iridocorneal angle.

The invention claimed is:

1. A method for measurement of at least one geometric value on a transparent or diffusive object by means of Time Domain Optical Coherence Tomography (TDOCT), comprising the steps of:

generating a radiation of short coherence length with a radiation source, splitting the radiation into a measurement arm and into at least two reference arms of a Michelson interferometer, forming reference arm beams are respectively in the at least two reference arms and guiding the reference beams to a rotating path length variation element, producing a change in delay time of the reference arm beams that is a function of a rotation of the path length variation element, bringing the transparent or diffusive object to be measured into the measurement arm, selecting fundamental optical delay times of the reference arms in such a way that an optical delay time difference of the beams in the at least two reference arms corresponds approximately to an optical delay time difference of the geometric value to be measured, and superposing radiation reflected at the transparent or diffusive object and in the reference arms together with interference, and respectively detecting resulting radiation interferences, further comprising the step of:

guiding the at least two reference arm beams of the reference arms to one and the same rotating path length variation element at a mutual spatial offset angle, wherein the guiding of the at least two reference arm beams of the reference arms to one and the same rotating path length variation element at a mutual spatial offset angle is done in such a way that the path length variation initially acts in the first reference arm and then in the second reference arm by virtue of the fact that a change in delay time caused by the path length variation element is successively impressed on the fundamental optical delay times in the reference arms as a result of which the radiation interferences defining the geometric value occur with temporal separation from one another.

2. The method as claimed in claim 1, wherein the radiation in the measurement arm in each case is focused on a first and a second layer boundary, defining the geometric value to be measured, on the transparent or diffusive object synchronously or periodically with the rotation.

3. The method as claimed in claim 1, wherein the path length variation element forms a regular polygon in cross section, the reference beams being reflected inside the path length variation element at least two of the lateral surfaces of the regular polygon.

4. The method as claimed in claim 1, further comprising arranging a prescribed optical structure upstream of the transparent or diffusive object to be measured, and imaging the reflection of the prescribed optical structure on the transparent or diffusive object, and comparing the reflection image with the prescribed optical structure for the purpose of determining a surface topography of the transparent or diffusive object as a further geometric value in order to determine a surface profile or a layer profile in addition to the thickness values of the transparent or diffusive object layers, and deflecting the beam of the measurement arm in a reflecting fashion to the transparent or diffusive object with the aid of a wavelength-selective mirror, the further radiation emanating from the prescribed optical structure having a different wavelength than the measurement arm beam, the wavelength-selective mirror transmitting the further radiation, and a pattern produced on the transparent or diffusive object surface by the further radiation being imaged on the other side of the wavelength-selective mirror in a backward extension of the axis of the measurement arm beam striking the transparent or diffusive object, and being detected, and producing the optical structure with a number of LEDs, the radiations of the LEDs preferably being focused onto a surface of the transparent or diffusive object.

5. The method as claimed in claim 1, wherein, in addition to the time domain optical coherence tomography, making use of a spectral domain optical coherence tomography with one and the same radiation source in order additionally to determine a topography in addition to the determination of the geometric value.

6. An apparatus for measurement of at least one geometric value of a transparent or diffusive object with the aid of a time domain optical coherence tomography, comprising:
- a Michelson interferometer having a radiation source of short coherence length and a measurement arm into which the transparent or diffusive object to be measured is brought,
- at least two reference arms with mutually differing fundamental optical path lengths corresponding to the at least one geometric value to be measured,
- a beam source respectively provided in the at least two reference arms for the purpose of providing reference arm beams, and
- a single path length variation element configured to act in both reference arms and to rotate about an axis of the path length variation element, wherein
- the at least two reference arm beams of the at least two reference arms are guided onto the path length variation element at a mutual offset angle in such a way that the path length variation initially acts in the first reference arm and then in the second reference arm by virtue of the fact that a path length variation is successively impressed on the fundamental optical path lengths.

7. The apparatus as claimed in claim 6, wherein the path length variation element has a number of lateral surfaces, while the element axis of the path length variation element is arranged parallel to the lateral surfaces and perpendicular to the axes of the reference arm beams.

8. The apparatus as claimed in claim 6, wherein the path length variation element is designed as a regular polygon in cross section, the reference beams being reflected inside the path length variation element at least two of the lateral surfaces of the regular polygon, and the lateral surfaces having at least one partial surface that acts to reflect approximately 100% of the reference arm beams, and each partial surface, beginning at each lateral surface corner being coated to reflect approximately 100% for only that beam section that can be reflected inside the path length variation element and forms an acute angle with the incident beam section belonging thereto, in order to achieve a beam guidance with the greatest possible loss reduction.

9. The apparatus as claimed in claim 6, further including a focusing unit arranged in the measurement arm of the Michelson interferometer and acts on the free measurement arm beam and whose focal point can be alternatingly focused on at least two different measuring points, it being possible to undertake the focusing onto the respective measuring points in a fashion synchronized with the rotation of the path variation element, and the focusing unit having a lens unit, there being arranged in the measuring beam path upstream or downstream of the lens unit, in a beam longitudinal region deviating substantially from a parallel beam configuration, an optical unit that moveable over the measuring beam cross section and with the aid of which it is possible to set a different beam configurations of the measuring beam for the purpose of producing a focal point displacement in a fashion synchronized with the rotation of the path variation element and, the optical unit having at least one transparent region of plane parallel design that can be brought into the measuring beam and has a prescribed optical length for the measurement beam that produces with the aid of the focusing unit a focal point displacement from one thickness limiting surface to the other, the at least one region being arranged in such a way that it can be located in the measuring beam during one of the active, alternating measurement times of the respective reference arm, and the optical unit being designed as a rotating circular disk with at least one transparent solid segment.

10. The apparatus as claimed in claim 6 wherein a number of illuminating radiation sources are arranged upstream of the transparent or diffusive object and can be imaged on the transparent or diffusive object surface with the reflection points of the illuminating radiation sources with the aid of an optical recording unit, and an evaluation unit with the aid of which the mutual spacings of the imaged reflection points can be set in relationship to the spacings of the radiation sources for the purpose of determining a surface curvature of the transparent or diffusive object surface as a further geometric value, and focusing elements that are arranged upstream of the radiation sources and with the aid of which the radiation of the illuminating radiation sources can be focused onto different regions in the transparent or diffusive object, it being possible in the case of the human eye as a transparent or diffusive object to use the focusing elements to focus onto the front corneal surface and/or onto the rear corneal surface and/or onto the lens front surface or onto the lens rear surface, the illuminating radiation sources being LEDs that emit a radiation of a different wavelength than the radiation source of the Michelson interferometer, and the focusing elements being cylindrical lenses, it being possible for the purpose of avoiding a multiplicity of cylindrical lenses to mount one or more rotating cylindrical lenses over the radiation sources.

11. The apparatus as claimed in claim 6, wherein radiation conductors with the aid of which the radiation of the reference arms and that of the measurement arm can be guided, and outcoupling and incoupling elements, arranged at the ends of the radiation conductors, with the aid of which the radiation guided or to be guided in the relevant radiation conductor can be coupled out or coupled in as a free space beam immediately upstream or downstream of optical components or upstream of the measurement object.

12. The apparatus as claimed in claim 10, wherein mutually different wavelengths of the short coherence radiation source and at least of a first number of illuminating radiation sources, by a wavelength-selective mirror in the measurement arm with the aid of which the beam of the short coherence radiation source can be reflected onto the object, and the radiation of the illumination radiation sources can be transmitted, and by an imaging unit for the radiation, that can be reflected by the object, of the illuminating radiation sources, the optical axis of the measurement arm coinciding with the optical axis of the imaging unit upstream of the object.

13. The apparatus as claimed in claim 9, wherein a 3×3 monomode fiber coupler, it being possible for the measurement radiation emanating from the 3×3 monomode fiber coupler to be guided in a first radiation conductor, and the monomode fiber coupler are connected to the Michelson radiation source via a second radiation conductor, to two reference arms via a third and fourth radiation conductor and to a first and second interference detector via a fifth and sixth radiation conductor, and the other end of the first radiation conductor being guided directly upstream of the focusing unit, there being arranged downstream of the focusing unit a wavelength-selective mirror with the aid of which the measurement radiation can be directed onto the transparent or diffusive object to be measured, and it being possible for the measurement radiation reflected by the transparent or diffusive object to be carried back into the focusing unit and into the first radiation conductor, and for illuminating radiation sources to be arranged between the wavelength-selective mirror and the transparent or diffusive object and an imaging system being arranged, in a rearward extension of the measuring beam on the side of the wavelength-selective mirror averted from the transparent or diffusive object, upstream of an optical evaluation unit for the illuminating radiation sources reflected on or in the object.

14. The apparatus as claimed in claim 6, wherein a spectral domain optical coherence tomograph is present in addition to the time domain optical coherence tomograph, the two tomographs operating with the aid of one and the same radiation source.

15. The apparatus as claimed in claim 14, wherein a spectrometer and a 4×4 monomode fiber coupler, it being possible for the measurement radiation for the time domain optical coherence tomograph and the spectral domain optical coherence tomograph to be guided in a first radiation conductor, and the monomode fiber coupler being connected to the radiation source via a second radiation conductor, to the two reference arms, which have a common path length variation element, via a third and a fourth radiation conductor, to a first and second interference detector via a fifth and sixth radiation conductor, to a third reference arm via a seventh radiation conductor, and to the spectrometer via an eighth radiation conductor.

* * * * *